United States Patent [19]
Palmai et al.

[11] Patent Number: 4,778,828

[45] Date of Patent: Oct. 18, 1988

[54] METHOD AND COMPOSITION FOR TREATING CATARACTS

[75] Inventors: Zolton Palmai; Gyula Nagy, both of Budapest, Hungary

[73] Assignee: New Vision Co. Ltd., Nassau, The Bahamas

[21] Appl. No.: 27,568

[22] Filed: Jul. 31, 1987

Related U.S. Application Data

[63] Continuation-in-part of Ser. No. 881,850, Jul. 3, 1986, abandoned.

[51] Int. Cl.$^4$ ............................................. A61K 31/045
[52] U.S. Cl. ..................................... 514/724; 514/912
[58] Field of Search ..................... 514/724, 912, 915

[56] References Cited

U.S. PATENT DOCUMENTS 3,226,295  12/1985  Goetz et al. ...................... 514/724
3,646,215  2/1972   Phillips ............................. 514/724

OTHER PUBLICATIONS

Chem. Abst. 103(24): 200771(j)(1985)–Attia et al.
Chem. Abst. 81: 16697(r)(1974)–Jurgens et al.
Drug & Cosmetic Industry–Apr., 1971–pp. 54, 56, 59, 134, 135, 136–138–Lee et al.

*Primary Examiner*—Douglas W. Robinson

[57] ABSTRACT

A non-toxic pharmaceutical composition which when applied to a patient with cataracts through preferably intravenous injection on a consecutive daily basis for a predetermined time period based upon the severity of the cataracts will serve to dissolve all the cataract and thereby restore commensurate lost vision to the patient due to the formation and presence of the cataract.

12 Claims, No Drawings

METHOD AND COMPOSITION FOR TREATING CATARACTS

BACKGROUND OF THE INVENTION

1. Field of the Invention

This invention relates to a curative composition and method of applying the same in the treatment of cataracts in a human patient and in animals.

2. Description of the Prior Art

It is well known in the field of medicine and particularly ophthalmology that the formation and existence of cataracts are damaging to the eyesight to the extent of partially or completely interfering with normal vision and in some cases, leaving severely afflicted patients completely blind. Modern medical technology has advanced to the point where cataracts, in some cases, can be removed through surgery. Such surgery involves the physical invasion of the eye proper and the removal of the cataract with the lens of the eye.

However, even with modern technological advancements in the medical profession, cataract surgery, even in the most successful operations, frequently results in the components of the eye and/or retina being distorted. This in turn results in affected vision of the patient even after removal of cataractous lens which can only be corrected through extremely strong glasses.

Accordingly, there is an obvious need in the medical profession for a means of effectively removing all the cataract in the majority of cases from the lens of the eye. Such a preferred method would in a normal situation eliminate the need for surgery with its associated risks like ablation of the retina, secondary cataract and retinal haemorrhage, etc. It is also the only possible way to eliminate the cataract when the patient can not be operated on due to diabetes, tetania, or high blood pressure, etc.

SUMMARY OF THE INVENTION

This invention relates to the formation and application of non-toxic pharmaceutical curative composition primarily designed for the treatment of cataracts in human patients but it is just as effective for the treatment of cataracts in animals. Specifically, the composition comprises a mixture of the following solid and liquid ingredients, wherein each of the ingredients in solid form or granular form are liquid soluble to effect the final resulting curative composition ready for administering to the patient in liquid form preferably.

The curative composition comprises a mixture of the following ingredients:

1. About 1 part of a alcohol of 14 to 19 carbon atoms, such as cetyl alcohol ($C_{16}H_{34}O$) and
2. About 10 parts of ethyl alcohol or 3 parts of ether added to and dissolved in
3. About 10 parts of a surfactant such as TWEENS, BRIJS, SPANS or others is added to
4. About 1,000 to 10,000 parts of 0.9% sodium chloride or other saline solution or water.

The aforementioned ingredients are mixed together in any order or all at once and thoroughly mixed or blended by physical stirring or the like to form the rsulting curative composition of the present invention ready for administration to a cataract patient in liquid form.

Once formulated in adequate quantities by the addition of the set forth ingredients in accordance with ratios equal to the above set forth weights and volume, the curative composition is administered preferably by intravenous injection. Administration of the subject curative composition occurs in extremely small dosages of 5 milliliters preferably administered through the aforementioned intravenous injection on a consecutive daily basis.

The length of time of administering the subject curative composition in terms of 5 milliliter dosages, each dose of 5 milliliters being administered once or twice each day for a consecutive day period, is dependent directly upon the severity of formation of the cataract.

The curative composition, in the aforementioned dosage, enters the circulatory system of the patient and, while having no toxic or harmful effect on any of the organs of the body, in the quantities administered, does serve to directly interact with the cataract to the extent of dissolving in whole the crystal-like bar formation of the cataract causing the cataract proper to dissolve. Removal of the dissolved cataract and remaining curative composition, still in a liquid state and in whatever form altered by interaction with the crystal-like bar formation of the cataract, partly occurs by natural functional operation of the eye such as being washed from the eye surface by tear formation and partly by metabolic process.

An important feature in the curative method of applying the subject composition is the daily examination of the cataract and eye proper to the extent of determining reduction in size of the cataract and/or complete removal thereof through the aforementioned dissolving property associated exclusively to the subject curative composition. The eye and associated cataract formation is to be examined on a consecutive daily basis and upon complete removal or dissolving of the cataract, treatment or continued administration of the composition is to be terminated. In certain instances, as set forth hereinafter, it has been determined that continued treatment for a preselected period of preferably two consecutive days after complete removal of the cataract is beneficial.

DESCRIPTION OF THE PREFERRED EMBODIMENT

The present invention relates to a curative composition and method of treatment of cataract patients utilizing the subject curative composition in the manner to be described in greater detail hereinafter through the presentation of certain examples. In each of the examples presented herein, the curative composition was administered in a liquid state wherein the curative composition comprises the mixture of the following ingredients of 1.2 milligrams of cetyl alcohol ($C_{16}H_{34}O$), and 12 milligrams of ethyl alcohol added to and dissolved in 48 milligrams of polysorbate 20 is added to 5 milliliters of 0.9% sodium chloride solution.

Obviously, larger volumes of the curative composition can be prepared in the same manner, or mixing and dissolving these aforementioned ingredients and solutions in the same ratios as indicated above. The order of mixing or addition of any of above ingredients to the other is not important.

In addition, thorough mixing of all the ingredients as set forth above in the designated ratios can occur through stirring or any other manual mixing technique. Prolonged or mechanized mixing or blending is not a requirement.

Examples to be set forth hereinafter are based on a testing of 35 individuals comprising both male and female patients and ranging in age from 50 years to 70 years. Some of the patients suffer from sugar diabetes which was believed to be the cause, at least in part, of the formation of cataract formations. Each of the patients included cataract formations on at least one eye, and some both eyes, in varying degrees of severity. The overall results of the experimentation indicated that vast improvement and/or complete dissolving of the cataract occurred in the least severe cases after a two day period of treatment as set forth hereinafter and usually after a 14 consecutive day period for the more severe cases.

EXAMPLE I

Three people, varying in age between 50 and 61 years, and generally determined to have the least severe cataract formations of the 35 patients tested were each administered 5 milliliters of the curative composition per day for 4 consecutive days by intravenous injection. For each of the four days the cataracts were examined. In each of the three patients, the cataract formation was completely dissolved after the first two consecutive days of treatment. Treatment was administered for an additional two days to insure complete dissolution of any remaining cataract formation remnants. All sight previously lost due to the cataract formation was restored in each of these three patients.

EXAMPLE II

Three of the 35 patients treated, and ranging in age from 59 to 70 years, were considered to have the more severe case of cataract formation. Each patient was administered 5 milliliters of the subject curative composition per day for 14 consecutive days. The cataract formation of each of those three patients was examined on a daily basis for the 14 consecutive days. At the end of the 14 day consecutive treatment period a majority of each cataract formation of each patient was dissolved to the extent of significant vision restoration to each of the three patients, when the initial loss of vision to each patient was attributed to cataract formation. It was further determined that each of those patients was diabetic and this fact was at least partially the cause for the initial formation of the cataract. Further, one of those three patients was totally blind due to the formation of cataracts on both eyes and vision was restored to the point of normalcy in this totally blind patient. It is further believed that the relatively long treatment period of 14 consecutive days was not due per se to the aged patients ranging from 59 to 70 years, but rather to the severity of the cataract formation. Also, the existence of diabetes in those three patients is not believed to reduce the effectiveness or necessarily prolong the period of treatment of the subject curative composition.

EXAMPLE III

The remaining 29 patients of the 35 patients originally tested varied in age from 51 to 69 and included both male and female patients, some of which were diabetic or had high blood pressure. Severity of the cataract formation on these 29 patients varied in severity. Each of the 29 patient were injected with 5 milliliters of the subject curative composition on a daily basis and the length of time of treatment of the 29 patients varied from 2 consecutive days of treatment to 10 consecutive days of treatment. The length of treatment was determined to be based directly on the severity of the cataract formation. The treatment resulted in the complete dissolution of the cataract formations and in the restoration of the vision originally lost due to the original formation of the cataract.

EXAMPLE IV

Animals specially horses, dogs and other pets, just like humans are inflicted with cataract for similar reasons.

The three dogs of 5 to 15 kilograms and the two race horses examined and treated by us had cataracts so severe that they could not see and were disoriented. We treated the dogs by administering daily 1 milliliter of our solution per kilogram of their weight and the horses with two 25 milliliter solution daily at 12 hours interval intravenously. After 7 days of this treatment the cataract at the center of the lens was dissolved and the blindness caused disorientation disappeared. We continued the treatment for 7 additional days after which all trace of the cataract disappeared from their eyes. They did not experience any toxicity or detrimental side effect.

CONCLUSIONS

Based on the experimentation with 35 patients ranging in age from 50 to 70, each varying in treatment period from 2 consecutive days to usually 14 consecutive days and each receiving 5 milliliters per day intravenous injection during the treatment period. The treatment resulted in the complete dissolution of the cataract formations and in the restoration of the vision originally lost due to the original formation of the cataract. No toxicity or harmful reaction occurred in any of the 35 patients and it was determined that the length of treatment period is directly dependent upon the severity of the formation of the cataract. The determination of the more severe cataract formation found in the older patients ranging in age from 59 to 70 was attributed to the length of time such formations had been in place resulting in a more severe formation and a longer treatment period.

Our experiments with animals have proven that our method of treating cataracts is very effective on animals too.

Now that the invention has been described, what is claimed is:

1. A method of treating cataracts on the eye of a human or other mammal comprising administering internally to said human or mammal a therapeutically effective amount of an alcohol having from 14 to 19 carbon atoms.

2. The method of claim 1 wherein a human is treated.

3. The method of claim 1 or 2 wherein the alcohol is 1-hexadecyl alcohol.

4. The method of claim 3 wherein the 1-hexadecyl alcohol is administered in the form of an emulsion.

5. The method of claim 3 wherein the alcohol is n-hexadecyl alcohol.

6. An ophthalmic composition for the treatment of cataracts in a human or other mammal comprising (a) about 1 part cetyl alcohol, (b) about 10 parts ethyl alcohol, (c) about 1,000 to 10,000 parts of a 0.9% sodium chloride solution and (d) about 0 to 140 parts of a surfactant.

7. The composition of claim 6 which additionally contains about 3 parts ether.

8. The composition of claim 6 or 7 wherein the surfactant is Tween 20.

9. An ophthalmic composition for the treatment of cataracts in a human or other mammal comprising (a) about 1.2 milligrams cetyl alcohol, (b) about 12 milligrams ethyl alcohol, (c) about 48 milligrams polysorbate 20, and (d) about 5 milliliters of 0.9% sodium chloride solution.

10. The composition of claim 9 which additionally contains about 3.6 milligrams of ether.

11. A method of treating cataracts in a human patient or other mammal comprising (a) injecting about 5 milliliters of the composition of claim 6, 7, 8, 9 or 10 intravenously on a daily basis until the cataracts have been completely dissolved.

12. The method of claim 11 wherein the treatment is continued for about 14 to about 16 days.

* * * * *